United States Patent
Schweitzer et al.

(10) Patent No.: US 7,409,299 B2
(45) Date of Patent: *Aug. 5, 2008

(54) METHOD FOR IDENTIFYING COMPONENTS OF A MIXTURE VIA SPECTRAL ANALYSIS

(75) Inventors: Robert Schweitzer, Pittsburgh, PA (US); Willem Windig, Rochester, NY (US); Patrick J. Treado, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 113 days.

This patent is subject to a terminal disclaimer.

(21) Appl. No.: 11/407,392

(22) Filed: Apr. 18, 2006

(65) Prior Publication Data

US 2007/0061091 A1    Mar. 15, 2007

Related U.S. Application Data

(63) Continuation of application No. 10/812,233, filed on Mar. 29, 2004, now Pat. No. 7,072,770.

(51) Int. Cl.
*G01N 31/00* (2006.01)
(52) U.S. Cl. .............. 702/25; 702/22; 702/23; 702/24
(58) Field of Classification Search .......... 702/25, 702/22, 23, 24
See application file for complete search history.

(56) References Cited

U.S. PATENT DOCUMENTS

| | | | |
|---|---|---|---|
| 4,660,151 A | 4/1987 | Chipman et al. | |
| 4,701,838 A | 10/1987 | Swinkels et al. | |
| 4,766,551 A | 8/1988 | Begley | |
| 4,885,697 A | 12/1989 | Huber | |
| 5,121,337 A | 6/1992 | Brown | |
| 5,121,338 A | 6/1992 | Lodder | |
| 5,124,932 A | 6/1992 | Lodder | |
| 5,311,445 A | 5/1994 | White | |
| 5,481,476 A | 1/1996 | Windig | |

(Continued)

OTHER PUBLICATIONS

Caetano et al. (1998) SPIE vol. 3499:257-269, Evaluation of the Importance of Non-Linear Spectral Mixing in Coniferous Forests.

(Continued)

*Primary Examiner*—John E. Barlow, Jr.
*Assistant Examiner*—Stephen J Cherry
(74) *Attorney, Agent, or Firm*—Duane Morris LLP

(57) ABSTRACT

Spectra data collected from a mixture defines an n-dimensional data space (n is the number of data points), and application of PCA techniques yields a subset of m-eigenvectors that effectively describe all variance in that data space. Each member of a library of known components is examined based by representing each library spectrum as a vector in the m-dimensional space. Target factor testing techniques yield an angle between this vector and the data space. Those library members that have the smallest angles are considered to be potential mixture members and are ranked accordingly. Every combination of the top y library members is considered as a potential solution and a multivariate least-squares solution is calculated using the mixture spectra for each of the potential solutions. A ranking algorithm is then applied and used to select the combination that is most likely the set of pure components in the mixture.

36 Claims, 12 Drawing Sheets

U.S. PATENT DOCUMENTS

| | | | |
|---|---|---|---|
| 5,606,164 | A | 2/1997 | Price et al. |
| 5,610,836 | A | 3/1997 | Alsmeyer et al. |
| 5,710,713 | A | 1/1998 | Wright et al. |
| 5,822,219 | A | 10/1998 | Chen et al. |
| 6,490,530 | B1 | 12/2002 | Wyatt |
| 6,549,861 | B1 | 4/2003 | Mark et al. |
| 6,584,413 | B1 | 6/2003 | Keenan et al. |
| 2004/0024539 | A1 | 2/2004 | Gard et al. |

OTHER PUBLICATIONS (1998) SPIE vol. 3499, Remote Sensing for Agriculture, Ecosystems, and Hydrology.

Rasmussen et al. (1979) Applied Spectroscopy vol. 33:371-376, Library Retrieval of Infrared Spectra Based on Detailed Intensity Information.

Guilment et al. (1994) Applied Spectroscopy vol. 48:320-326, Infrared Chemical Micro-Imaging Assisted by Interactive Self-Modeling Multivariate Analysis.

Malinowski (1991) Factor Analysis In Chemistry, 2d Ed, published by John Wiley & Sons, Inc.

Press et al., Numerical Recipes in C, The Art of Scientific Computing, 2d Ed; originally published 1992—latest publication date 2002; published by Press Syndicate of the University of Cambridge.

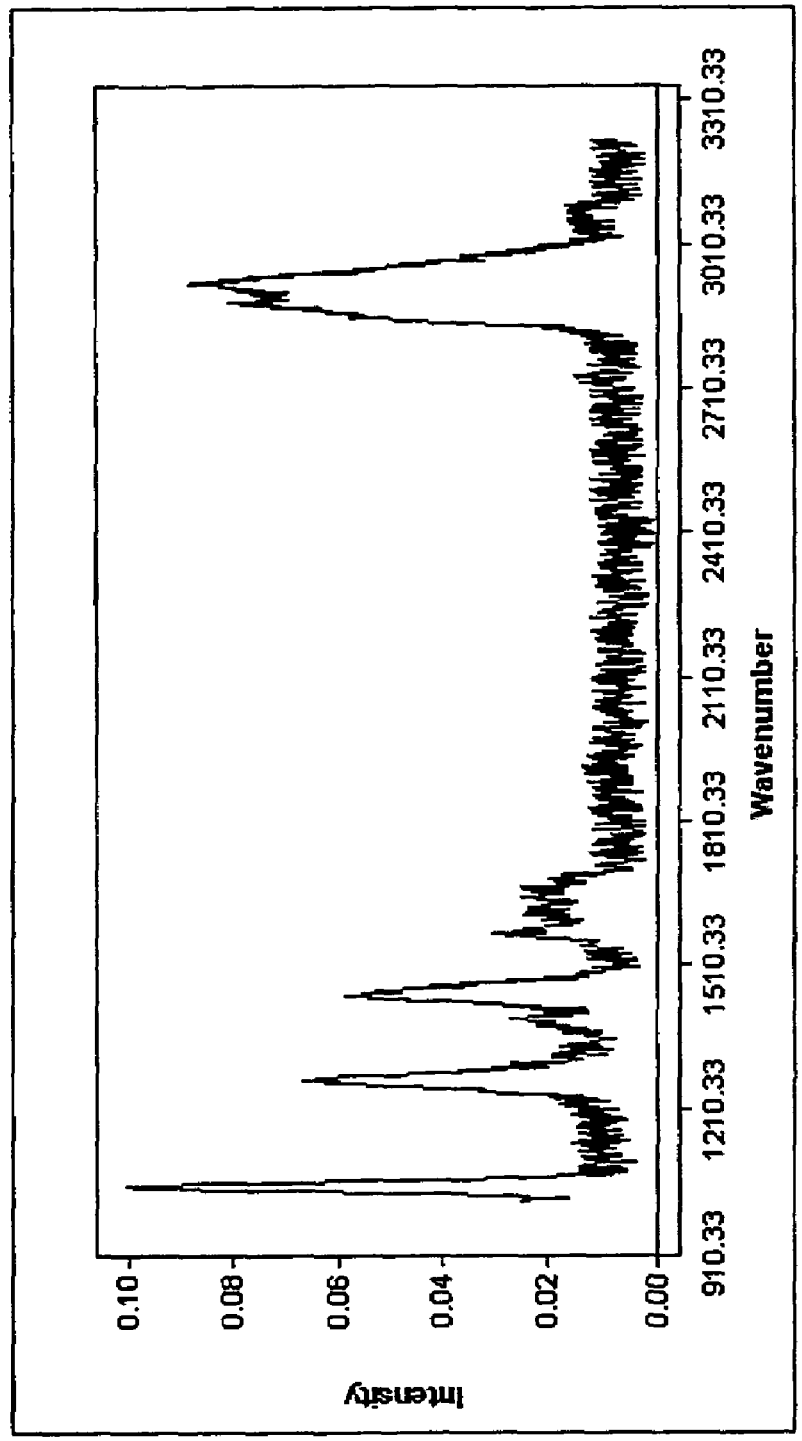

All Mixture Spectra

Bacillus Pumilis

Bacillus Subtilis

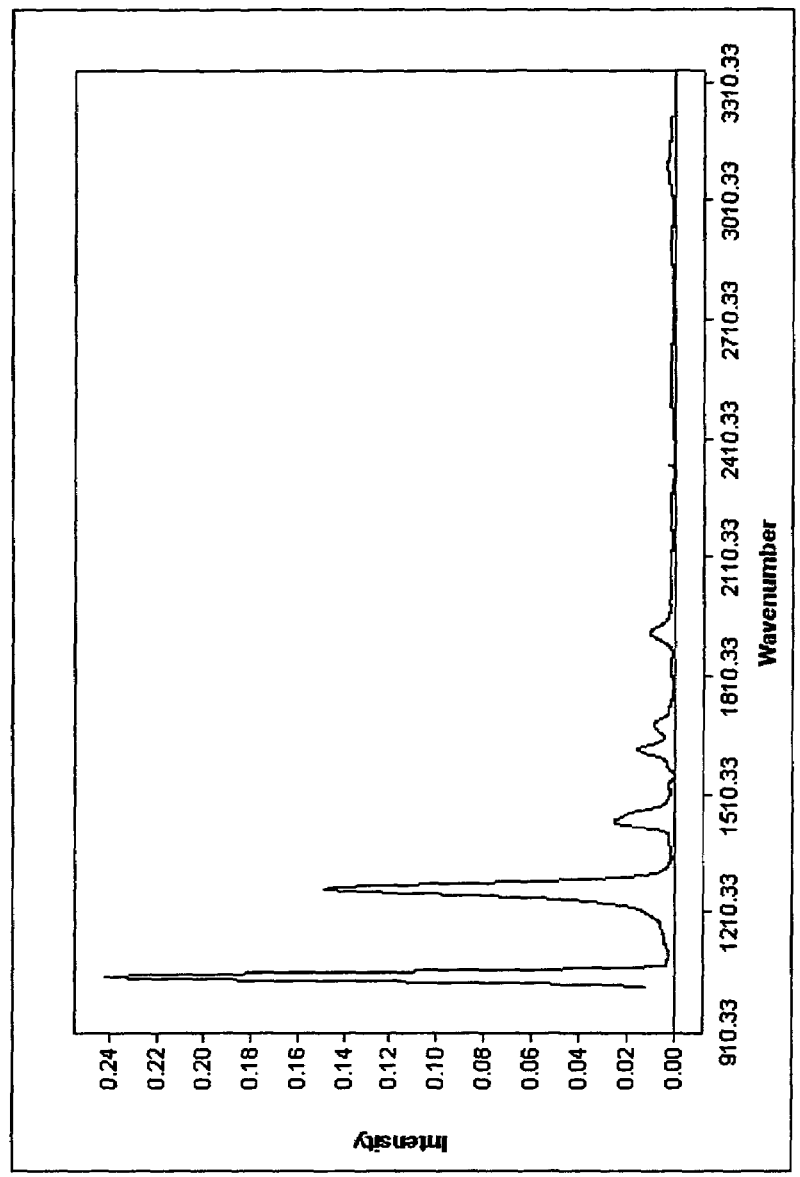
Fig. 2e Baking Soda

Physical Image of the Mixture

First Mixture Spectrum

All Mixture Spectra

Cane Sugar

Microcrystalline Cellulose

Corn Starch

METHOD FOR IDENTIFYING COMPONENTS OF A MIXTURE VIA SPECTRAL ANALYSIS

RELATED APPLICATIONS

This application is a continuation of Ser. No. 10/812,233, filed Mar. 29, 2004 and claims priority benefit to U.S. Pat. No. 7,072,770 entitled "METHOD FOR IDENTIFYING COMPONENTS OF A MIXTURE VIA SPECTRAL ANALYSIS," which is incorporated herein by reference in its entirety.

FIELD OF THE INVENTION

The present invention is directed generally toward the field of spectral analysis and, more particularly, toward an improved method of identifying unknown components of a mixture from a set of spectra collected from the mixture using a spectral library including potential candidates.

BACKGROUND OF THE INVENTION

It is becoming increasingly important and urgent to rapidly and accurately identify toxic materials or pathogens with a high degree of reliability, particularly when the toxins/pathogens may be purposefully or inadvertently mixed with other materials. In uncontrolled environments, such as the atmosphere, a wide variety of airborne organic particles from humans, plants and animals occur naturally. Many of these naturally occurring organic particles appear similar to some toxins and pathogens, even at a genetic level. It is important to be able to distinguish between these organic particles and the toxins/pathogens.

In cases where toxins and/or pathogens are purposely used to inflict harm or damage, they are typically mixed with so called "masking agents" to conceal their identity. These masking agents are used to trick various detection methods and apparatus to overlook or be unable to distinguish the toxins/pathogens mixed therewith. This is a recurring concern for homeland security where the malicious use of toxins and/or infectious pathogens may disrupt the nation's air, water and/or food supplies. Additionally, certain businesses and industries could also benefit from the rapid and accurate identification of the components of mixtures and materials. One such industry that comes to mind is the drug manufacturing industry, where the identification of mixture composition could aid in preventing the alteration of prescription and non-prescription drugs.

One known method for identifying materials and organic substances contained within a mixture is to measure the absorbance, transmission, reflectance or emission of each component of the given mixture as a function of the wavelength or frequency of the illuminating or scattered light transmitted through the mixture. This, of course, requires that the mixture be separable into its component parts. Such measurements as a function of wavelength or frequency produce a plot that is generally referred to as a spectrum. The spectra of the components of a given mixture, material or object, i.e., a sample spectra, can be identified by comparing the sample spectra to a set of reference spectra that have been individually collected for a set of known elements or materials. The set of reference spectra are typically referred to as a spectral library, and the process of comparing the sample spectra to the spectral library is generally termed a spectral library search. Spectral library searches have been described in the literature for many years, and are widely used today. Spectral library searches using infrared (approximately 750 nm to 1000 µm wavelength), Raman, fluorescence or near infrared (approximately 750 nm to 2500 nm wavelength) transmissions are well suited to identify many materials due to the rich set of detailed features these spectroscopy techniques generally produce. The above-identified spectroscopy techniques provide a rich fingerprint of the various pure entities that are currently used to identify them in mixtures which are separable into its component parts via spectral library searching.

While spectral library searching is a widely used method of determining the composition of mixtures, there are a number of factors that can complicate the process of spectral library searching. In an ideal world, the spectrum of a mixture, material, or component part thereof would only contain information that corresponds to the chemical constituency of that mixture, material, or component part. However, in actuality, most spectra also contain information that is related to the instrument response function of the instrument used to collect the spectra. Various known correctional algorithms are typically applied to the raw spectral data in an attempt to minimize the amount of instrumental information contained in both the reference and sample spectra.

Another problem with spectral library searching is that many samples of interest submitted for identification are mixtures rather than pure components. Spectral library searching can only be used to identify pure components. The number of possible mixtures of even a limited multi-component system is very large. The spectrum of a mixture typically differs significantly from the spectra of the pure components that comprise the mixture. Since a typical spectral library stores only spectra of pure components, the current, commercially available spectral library packages are generally unable to identify the components of any given mixture that a user might analyze. Therefore, a method to clearly delineate and identify various materials and, more specifically, toxins and pathogens, when they occur in mixtures is both a timely and important problem that is addressed by the present invention.

Several multivariate statistical techniques are currently available that allow a data analyst to identify components of a particular mixture from their spectra. One such technique is the "target factor testing" approach that has been developed by Malinowski (see E. R. Malinowski, *Factor Analysis in Chemistry*, Wiley-Interscience, New York, 1991), the disclosure of which is incorporated by reference herein. Target factor testing results in a ranking of the target spectra, i.e., those spectra that are considered as potential candidates of the mixture, and reports the top x targets as the pure components of the mixture. It has been found, however, that there are many cases where the actual components of the mixture are ranked high in the candidate list, but are not ranked within the top x matches (where x is the number of pure components in the mixture). Thus, target factor testing has certain disadvantages when used to identify toxins and biological pathogens in mixtures, since a high degree of reliability and accuracy is generally desired.

The present invention is directed toward overcoming one or more of the above-mentioned problems.

SUMMARY OF THE INVENTION

The present invention combines the generality of typical spectral library searching with the ability of target factor testing to identify the components contained within a mixture. Current evaluations of the inventive approach as applied to toxin and pathogen detection have proven to provide superior detection, identification, reproducibility and reliability than has been possible with other known alternative spectral unmixing analysis methods.

The method of the present invention allows the components of a mixture to be identified from a set of spectra collected from the mixture sample. The present invention can be applied to the spectra derived from several arbitrary points of the sample, as obtained with a point focus spectrometer, or from various regions in a field of view, as obtained with a full field of view imaging spectrometer. It can also be successfully applied in dynamic situations where it is desired to analyze trends in the composition of a mixture over a period of time. The present invention has been successfully tested via the identification of components of mixtures of common household materials, laboratory chemicals, and a variety of biological species (primarily *Bacillus*) from their Raman spectra.

According to the spectral unmixing method of the present invention, a set of spectral data is collected from a mixture (i.e., mixture spectra). The mixture can be a gas, liquid, solid, powder, etc. The mixture spectra are corrected to remove instrumental artifacts, including fluorescence and baseline effects. The collected mixture spectra define an n-dimensional data space, where n is the number of spectral points in the spectra. Principal component analysis (PCA) techniques are applied to the n-dimensional data space to reduce the dimensionality of the data space. The dimensionality reduction step results in the selection of m eigenvectors as coordinate axes in the new data space. The members of a spectral library of known, pure components are compared to the reduced dimensionality data space generated from the mixture spectra using target factor testing techniques. Each library spectrum is projected as a vector in the reduced m-dimensional data space, and target factor testing results in an angle between the library vector and the data space for each spectral library member by calculating the angle between the library member and the projected library spectrum. Those spectral library members that have the smallest angles with the data space are considered to be potential members, or candidates, of the mixture and are submitted for further testing in accordance with the inventive method. The spectral library members are ranked and every combination of the top y members is considered as a potential solution to the composition of the mixture. As will be discussed later, in a preferred embodiment, y has a value of 10 in these applications. However, this can be generalized to as many components as can be handled by the computing capabilities employed for this analysis. A multivariate least-squares solution is then calculated using the mixture spectra for each of the candidate combinations. Finally, a ranking algorithm is applied to each combination and is used to select the combination that is most likely the set of pure components in the mixture, and thus identify the components of the mixture.

The identification of the components of the mixture is typically performed on a surface upon which the mixture is located. This results in the mixture being spread out or located over some spatial area which is then probed by the spectroscopic method. The spectral data can thereby consist of sets of spectral data at different spatial positions which will define the n-dimensional data space. The small, often subtle, spatial variations in this n-dimensional data space allow greater sensitivity to deconvolve or unmix the components of the mixture.

In one form, another set of spectral data are obtained from the mixture at a later point in time, such that the another set of spectral data is separated from the set of spectral data by a time interval. The collected another spectral data set defines an n-dimensional data space, and the inventive spectral unmixing method described herein is applied to the another spectral data set to determine the set of components in the mixture at the later point in time. The identified components of the mixture from both the set of spectral data and the another set of spectral data can be utilized to analyze trends in the composition of the mixture over the time interval. The speed at which the inventive method identifies the components of the mixture allows the inventive method to be used in such dynamic spectral unmixing applications where the sampling of a mixture occurs in defined or random intervals.

In another form, different sets of spectral data are obtained from the mixture at different points in time. The different sets of spectral data (e.g., two or more) are combined into a combined spectral data set, and the inventive spectral unmixing method described herein applied to the combined spectral data set to determine the composition of the mixture. By combining the spectral data sets, it is possible to obtain better results than if each spectral data set were analyzed individually.

It is an object of the present invention to accurately and rapidly identify the various components contained in a mixture.

It is an additional object of the present invention to accurately and rapidly identify the various components in a mixture at different spatial locations.

It is a further object of the present invention to analyze trends in the composition of a mixture over a period of time.

Other objects, aspects and advantages of the present invention can be obtained from a study of the specification, the drawings, and the appended claims.

BRIEF DESCRIPTION OF THE DRAWINGS

FIG. 2a is a spectral plot of a first mixture spectrum in a set of mathematically generated mixture spectra containing *Bacillus Pumilis, Bacillus Subtilis* and Baking Soda, with random wavelength and intensity independent noise added at a level of 1%;

FIG. 2e is a spectral plot of Baking Soda;

DETAILED DESCRIPTION OF THE INVENTION

The present invention requires the existence of a spectral library of reference materials. The spectral library includes a set of reference spectra that have been individually collected for a set of known elements. As used herein, the term element refers to atomic elements, materials, mixtures, compositions, chemical species, etc. The spectral library will be used in accordance with the method of the present invention as described herein to identify the components in a mixture.

Figure 1:
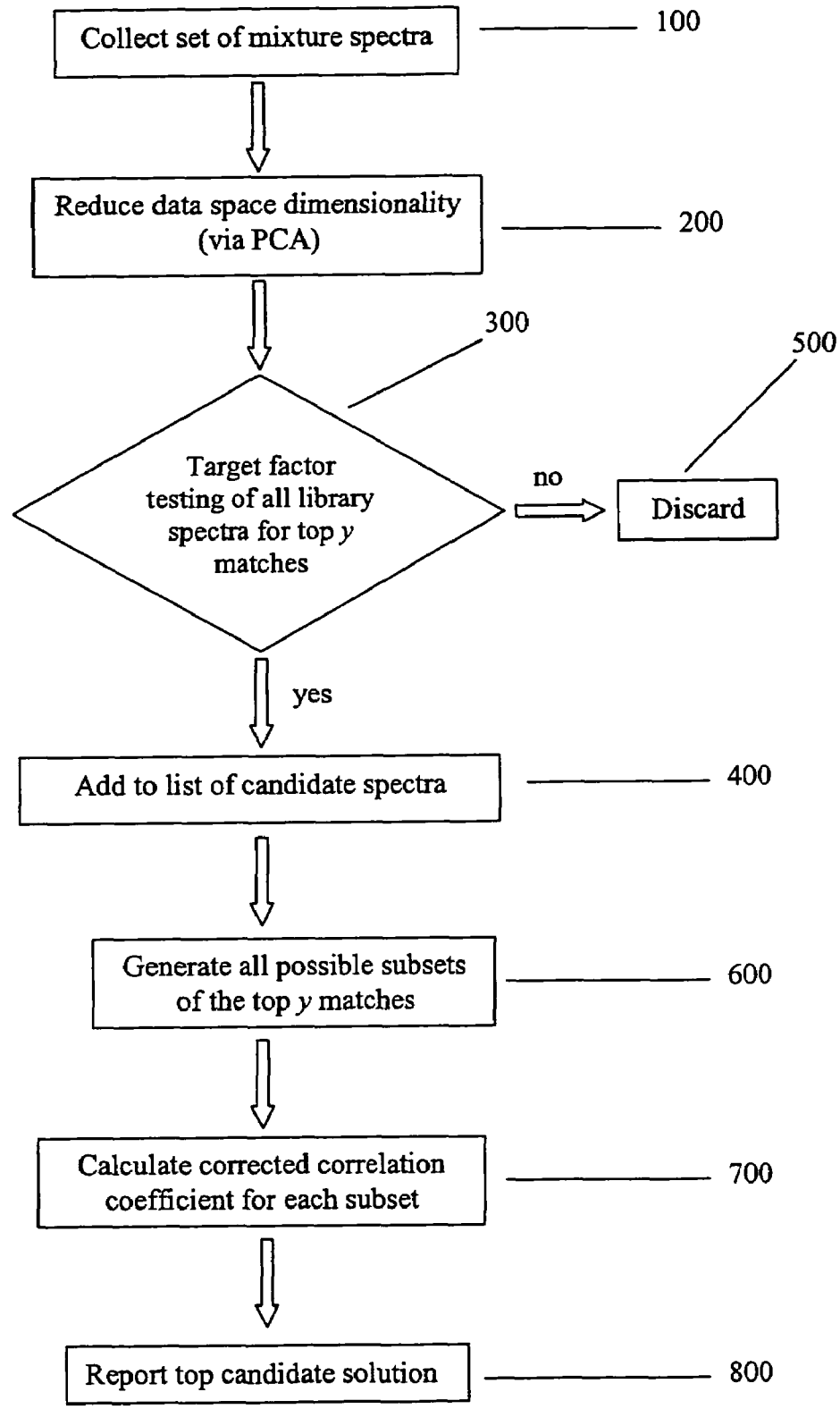
FIG. 1 is a general flow chart of the spectral unmixing method in accordance with the present invention.

As shown in the flow chart of FIG. 1, the first step of the inventive method includes the collection of a set of spectra taken at various points or at particular times from a mixture sample (mixture spectra), as shown at block 100. The mixture spectra can be collected using various spectroscopical techniques, such as, but not limited to, infrared, Raman, florescence and near infrared spectroscopy techniques. The mixture spectra, as well as the library spectra, should be corrected to remove all signals and information that are not due to the chemical compositions of the mixture sample and known elements/materials. These include various instrumental effects, such as the transmission of optical elements, the responsivity of the detector, and any other non-desired sample effects due to the instrument utilized to collect the spectra, for example, fluorescence in the case of Raman spectra. The mixture spectra, as well as the library spectra, may be corrected to remove instrumental artifacts using any of a variety of known correction methods. However, one skilled in the art will appreciate that uncorrected spectra may also be utilized to practice the inventive method such as, for example, when second derivative spectra are used, without departing from the spirit and scope of the present invention.

The key to the inventive spectral unmixing approach is that the mixture be composed of non-uniformly admixed substances. This arises from random and/or statistical fluctuations in the mixture of even admixed substances that will appear at various degrees of magnification. For example, granular mixtures will exhibit variations on the scale of the grain size as one moves from one grain to another grain. However, sufficiently far away when the individual grains cannot be distinguished, a uniform mixture may appear. The degree to which the different grains are uniformly blended throughout the mixture, however, will determine whether this admixture appears to be uniform.

In most practical cases, such non-uniformities are common and thereby will yield to the inventive method, providing that the magnification used to examine the mixture is sufficient to resolve these non-uniformities. Choosing the sampling regions to obtain the mixture spectra is thereby important, and the image of the sample can be used to target specific areas to identify regions of spectra. Obtaining spectral data from an entire field of view with an imaging spectrometer, i.e., one that acquires spectra over an entire field of view, is preferred since spectra from all regions of the sample under observation are acquired simultaneously and become part of the mixture spectra, or data set, to be analyzed. In this latter approach to collecting spectral data over an entire field of view, one does not have to second-guess which regions may be important. The spectral variations found in every pixel of the image will be available and accessible for analysis.

The magnification with which the spectra are collected, i.e., the spatial resolution, must be such that each mixture spectrum collected has varying percentages of the pure components represented in each spectrum (see J. Guilment, S. Markel and W. Windig, *Infrared Chemical Micro-Imaging Assisted by Interactive Self-Modeling Multivariate Analysis*, Applied Spectroscopy, vol. 48, no. 3, pp 320-326, 1994), the disclosure of which is incorporated by reference herein. If the spatial resolution is high enough, one could get pure component spectra. However, that is generally not practical or even possible. The inventive method will work even though the spectra collected do not represent the pure components in the mixture. The only stipulation is that the spatial resolution must not be so low that the spectra are identical and represent totally homogenous mixtures at every data point. In other words, the concentrations of the components within the mixtures must (and usually do) vary slightly over the regions sampled. Collection or deposition methods that bring out or emphasize such inhomogeneities in a mixture on the relevant scale for inspection and spectral sampling will further improve the sensitivity, speed and/or accuracy of the inventive method.

The collected set of mixture spectra generally define an n-dimensional data space, where n is the number of spectral points in the mixture spectra. After the mixture spectra have been corrected to remove instrumental artifacts, the next step of the inventive method is to apply conventional principal component analysis (PCA) techniques to the set of mixture spectra to generate m eigenvectors, as shown at block 200. PCA techniques are well known in the relevant art and, accordingly, a detailed description of such techniques is not necessary. This step allows a reduction in the dimensionality of the data space and allows the representation of each of the mixture spectra as a vector in the m-dimensional space, where m is selected as the number of eigenvectors needed to explain 99% of the variance of the data. The key equation utilized in applying principal component analysis (PCA) techniques is:

$$\text{Data}_{pxn} = U_{pxn} * W_{nxn} * V_{nxn}^T \quad \text{(Eq. 1)},$$

where Data is the input data matrix with p rows and n columns, W is a diagonal matrix with positive or zero valued elements that correspond to the n eigenvalues of the input data matrix, $V^T$, the so-called loadings, is a transpose matrix related to the diagonal matrix W, and U, the so-called scores, is a matrix that corresponds to the set of n eigenvectors for the input data matrix. Note, that as already mentioned, only m of the n eigenvectors are used. While PCA techniques are utilized herein to scale the set of mixture spectra, it should be understood that singular value decomposition (SVD) techniques, as well as other scaling techniques, can be utilized without departing from the spirit and scope of the present invention. More details on the SVD algorithm, which is the core of PCA, can be obtained by consulting a mathematical text such as Numerical Recipes (see *Numerical Recipes in C*, Cambridge University Press, Cambridge, 1999), the disclosure of which is incorporated by reference herein.

Conventional target factor testing techniques can be applied to the set of m eigenvectors to determine the top y candidates of the mixture, as shown at block 300. Target factor testing techniques are well known in the relevant art and, accordingly, a detailed description of such techniques is not necessary. In applying target factor testing, each library spectrum is represented as a vector in the n-dimensional data space, and the angle of projection of each library spectrum with mixture data space is calculated. This calculation involves taking the dot product of the library vector with the n-dimensional data space. More specifically, this calculation is performed by taking the dot product of the library spectrum $lib_j$ with each eigenvector $V_{j,i}$ (also termed the loading vector or principal component), in accordance with the following equation:

$$s_i \equiv \sum_{j=1}^{n} lib_j * V_{j,i}, \quad \text{(Eq. 2)}$$

where j ranges over the number of spectral points in each library spectrum (equivalent to the number of points in each eigenvector $V_{j,i}$) and i is the number of eigenvectors used to represent the mixture data space. Eq. 2 assumes that the sum of squares of the matrix V is equal to 1, and the sum of squares of $lib_j$ is also equal to 1. The resultant of each dot product is a scalar $s_i$. The resulting scalars for a given library spectrum are combined by taking the square root of the sum of the squares of the scalars, in accordance with the following equation:

$$s_{avg} \equiv \sqrt{\sum_{i=1}^{m} s_i * s_i}, \qquad \text{(Eq. 3)}$$

where i ranges over the number of eigenvectors used to represent the mixture data space.

The resulting scalar $s_{avg}$ represents the cosine of the angle of the library spectrum with the mixture data space. If the value of the resulting scalar is 1.0, the library spectrum maps perfectly into the mixture data space. As the resulting scalar $s_{avg}$, i.e., the cosine of the angle, becomes closer to zero, the fit of the library spectrum into the mixture data space becomes increasingly worse. Accordingly, an angle of 0-degrees represents a perfect fit of the library spectrum into the mixture data space, and indicates an element that is a likely component of the mixture. The library spectra are then ranked by their angle of projection into the mixture data space, i.e., the closer the resulting scalar $s_{avg}$ is to 1.0, the higher the library spectrum is ranked. However, it has been found that this ranking of the library spectra via target factor testing techniques is not sufficient to generally yield correct identification of the components of a mixture. Thus, the present invention requires a further series of operations in order to accurately identify the components of the mixture.

In the next step of the inventive method, the top y library spectra are selected as potential components or candidates of the mixture and are submitted for further testing, as shown at block 400. If the library spectrum is not within the top y matches, it is discarded at block 500. All possible subsets, or combinations, of the top y matches are generated, as shown at block 600, and a series of operations are then applied to every possible combination of these top y matches to develop a ranking criterion for each combination. The number of possible combinations for the top y matches is equal to the formula $2^y-1$.

In a preferred embodiment of the present invention, y is set equal to 10, such that the inventive method performs the series of operations on every possible combination of the top 10 matches, as shown at block 700. It has been found herein that the actual components of a mixture will typically be included in the top 10 matches developed by conventional target factor testing. Thus, in the preferred embodiment y is set equal to 10. For cases where matches are not found in the top 10, y can be increased to be greater than 10.

In the particular case with y set to equal to 10, there will be, 10, 45, 120, 210, 252, 210, 120, 45, 10 and 1 (=1023) combinations, or candidate solutions, generated for the 1-, 2-, 3-, 4-, 5-, 6-, 7-, 8-, 9-, and 10-component solutions, respectively. For each combination, a series of operations is performed that generates the ranking, or scalar, criterion, i.e., corrected correlation coefficient CorrectCorrCoef, that is used to select the most likely combination, i.e., components of the mixture, as shown at block 700. The series of operations performed at block 700 is as follows.

The first step in generating the ranking, or scalar, criterion is to calculate a projected library spectrum for each pure component library spectrum in a given candidate solution. The projected library spectrum is calculated in two steps. The first step uses the known mixture spectra and the known pure component library spectra in the set of candidate spectra to calculate the relative concentrations or contributions of each of the component library spectra. In equation form, the mixture spectra can be represented as follows:

$$M_{axb} = C_{axd} * L_{dxb} + E_{axb} \qquad \text{(Eq. 4)},$$

where M is the mixture data set with a rows of mixture spectra and b columns of variables, C is the unknown contributions or concentrations, L is a matrix with d rows of candidate library spectra and b columns of variables, and E represents an error matrix with a rows and b columns. The estimate of the concentrations $\hat{C}$ is calculated using a classical least-squares analysis. The least-squares procedure calculates a solution for Eq. 4 in which the error matrix E is minimized. The equation for calculating $\hat{C}$ is as follows:

$$\hat{C} = ML^T(LL^T)^{-1} \qquad \text{(Eq. 5)}.$$

The second step uses the calculated concentrations $\hat{C}$ and the known mixture spectra M to calculate the projected library spectra $\hat{L}$, in accordance with the following equation:

$$\hat{L} = (\hat{C}^T\hat{C})^{-1}\hat{C}^TM \qquad \text{(Eq. 6)}.$$

If the projected (calculated) library spectra $\hat{L}$ are very similar to the actual library spectra L, the candidate solution (set of suggested library spectra) is most likely correct. Similarly, if the projected (calculated) library spectra $\hat{L}$ are dissimilar to the actual library spectra L, the candidate solution (set of suggested library spectra) is most likely not correct. To measure the similarity of the actual library spectra L to the projected (calculated) library spectra $\hat{L}$, the correlation coefficient CorrCoef of each projected (calculated) library spectrum $\hat{L}$ with its actual library spectrum L is calculated. The correlation coefficient CorrCoef is the dot product of the projected library spectrum $\hat{L}$ with the actual library spectrum L, divided by the multiplication of the dot product of the projected library spectrum $\hat{L}$ with itself and the dot product of the actual library spectrum L with itself, in accordance with the following equation.

$$CorrCoef \equiv \frac{\sum_{i=1}^{n} \hat{L}_i * L_i}{\sum_{i=1}^{n} \hat{L}_i * \hat{L}_i \sum_{i=1}^{n} L_i * L_i}, \qquad \text{(Eq. 7)}$$

where i ranges over the number of spectral points, $\hat{L}$ is the projected library spectrum, and L is the actual library spectrum. From the resulting correlation coefficient CorrCoef for each library spectrum within a candidate solution, the square root of the sum of the squares of the correlation coefficients for a potential candidate solution divided by the number of members in the candidate solution is calculated to develop a cumulative correlation coefficient value CumCorrCoef as follows.

$$CumCorrCoef \equiv \sqrt{\frac{\sum_{i=1}^{x} CorrCoef_i * CorrCoef_i}{x}}, \qquad \text{(Eq. 8)}$$

where i ranges over the number of components x in the candidate solution. This cumulative correlation coefficient value CumCorrCoef is the basic criterion used to judge among multiple candidate solutions in order to determine the top candidate solution, which represents the most likely components of the mixture.

To prune out unreasonable solutions, any candidate solution in which one of the components is calculated to have negative concentrations in the mixture spectra is eliminated. This step is further refined by calculating the ratio of the maximum positive concentration to the average of the sum of the absolute values of the negative concentrations, and eliminating that candidate solution if this ratio is less than 4.0. This refinement allows the case to be captured in which only one or a small number of mixture spectra have significant concentrations of a given component. The Ratio is calculated according to the following equation.

$$\text{Ratio} \equiv \frac{MaxPos}{\sum_{i=1}^{z} |Conc_i|/z}, \quad \text{(Eq. 9)}$$

where z is the number of concentrations that are negative, MaxPos is the value of the concentration value with the highest positive concentration, and $Conc_i$ are the set of concentration values that are negative. The inventive method is further enhanced by squaring the cumulative correlation coefficient value CumCorrCoef (to convert it to variance) and multiplying it by the cumulative eigenvalues for each candidate solution, as follows.

$$\text{CorrectCorrCoef} = \text{CumCorrCoef} \ast \text{CumCorrCoef} \ast \text{CumEigen}_i \quad \text{(Eq. 10)},$$

where i is the number of components in the candidate solution (and the number of eigenvalues to use for the sum of the cumulative eigenvalues). Note that the cumulative eigenvalues $\text{CumEigen}_i$ are reported and used as a decimal percentage based on the number of calculated eigenvectors needed to explain 99.9% of the variance.

The cumulative eigenvalues, or cumulative variance, are calculated as follows. First, the eigenvalues of the mean centered data set are obtained. It should be noted that the mixture spectra cannot be normalized for this procedure, since normalization of the mixture spectra will result in a rank of the data set of one less than the number of components in the mixture. The eigenvalues are then normalized so that the sum of all eigenvalues is equal to 1, as follows:

$$\lambda_{i(scaled)} = \frac{\lambda_i}{\sum_{j=1}^{m} \lambda_j}, \quad \text{(Eq. 11)}$$

where $\lambda_{i(scaled)}$ is the eigenvalue scaled by the sum of the eigenvalues, and $\lambda$ is the eigenvalue of the centered data. The cumulative eigenvalues CumEigen are then calculated as follows:

$$CumEigen_i = \lambda_{i(cumulative)} = \sum_{j=1}^{i} \lambda_{j(scaled)}, \quad \text{(Eq. 12)}$$

where the values for i range from 1 to m.

The additional term of the variance was added since, without it, in some cases a candidate solution with not enough components may have been chosen. As mentioned above, the cumulative eigenvalues, or cumulative variance, are scaled to have a maximum of 1. For example, for a three component mixture the diagnostic value (without the cumulative variance) may incorrectly show a maximum for a solution with two components. However, the cumulative variance (cumulative eigenvalues) will be significant lower for this two component solution than for the correct three component solution. By combining the cumulative eigenvalues (cumulative variance) with the diagnostic value as shown in Eq. 10, the three component solution will produce a higher corrected correlation coefficient CorrectCorrCoef and minimize the problem of underestimating the number of components.

The resulting ranking criterion, i.e., the corrected correlation coefficient CorrectCorrCoef, is used to select the most likely candidate solution. The correct candidate solution is the one with highest corrected correlation coefficient CorrectCorrCoef, as shown at block 800. The inventive method has been tested on a number of experimental and simulated data sets with excellent results, as shown below.

There can be cases where larger numbers of actual components in the mixture arise. In such cases, it is likely that some logical neighborhood in the sample will exhibit a smaller number of components. For this case, a data set can be calculated over each neighborhood, and these algorithms applied independently to each. The final set of compounds present in the mixture is the collective set of these local regions.

EXAMPLE 1

One such simulated data set is a set of 22 mixture spectra (with 1269 spectral points from 1020.75 to 3229.20 cm$^{-1}$) that was generated by mathematically combining various multiples of three experimental spectra of *Bacillus Pumilis*, *Bacillus Subtilis* and Baking Soda, with the contributions of each ranging from 30.0 to 38.333%, and with random wavelength and intensity independent noise being added at a level of 1%. The spectra library for these examples consisted of 18-150 spectra of known pure components. Since the experimental mixture spectra were generated mathematically, the steps of collecting the mixture spectra and removing instrumental artifacts can be omitted. The next step of the inventive method uses conventional target factor testing to return the top 10 matches (y=10), where an angle of 0-degrees represents a perfect match.

TABLE 1

| Spectral Library Entry | Angle |
| --- | --- |
| *Bacillus Pumilis* | 18.60 |
| *Bacillus Subtilis* | 21.67 |
| *Bacillus Cereus* | 25.24 |
| *Bacillus Anthracis* | 25.81 |
| *Clostridium Sporogenes* | 25.86 |
| Baking Soda | 25.95 |
| Carboxymethyl Cellulose | 26.40 |
| Bisquick | 27.36 |
| Flour | 28.46 |
| *Bacillus Thuriengis* | 29.88 |

As can be seen from Table 1, Baking Soda is not among the top three matches. Thus, traditional target factor testing would result in an incorrect identification of the components of the mixture. Applying the remaining steps of the inventive method yield corrected correlation coefficient values CorrectCorrCoef of 0.1978, 0.3134, 0.3570, 0.3250, and 0.2985 as the top solutions for mixtures with one through five components, respectively (where a value of 1.0 represents a perfect match). The top five candidate solutions calculated in accordance with the inventive method are shown in Table 2 below.

TABLE 2

| Components | CCC Value |
|---|---|
| *Bacillus Pumilis, Bacillus Subtilis*, Baking Soda | 0.3570 |
| *Bacillus Pumilis, Bacillus Subtilis, Bacillus Cereus*, Baking Soda | 0.3250 |
| *Bacillus Pumilis, Bacillus Subtilis, Clostridium Sporogenes*, Baking Soda | 0.3223 |
| *Bacillus Pumilis, Bacillus Subtilis*, Baking Soda, Carboxymethyl Cellulose | 0.3184 |
| *Bacillus Subtilis, Bacillus Cereus*, Baking Soda | 0.3160 |

As can be seen from Table 2, the best match occurs for a mixture with three components, and the three-component system with the best match is *Bacillus Pumilis, Bacillus Subtilis*, and Baking Soda. The corrected correlation coefficient values CorrectCorrCoef calculated are low because the mixture spectra are very noisy (a perfect match would have a value of 1.0). In spite of this, the inventive method is able to return the correct result for this example.

Figure 2B:
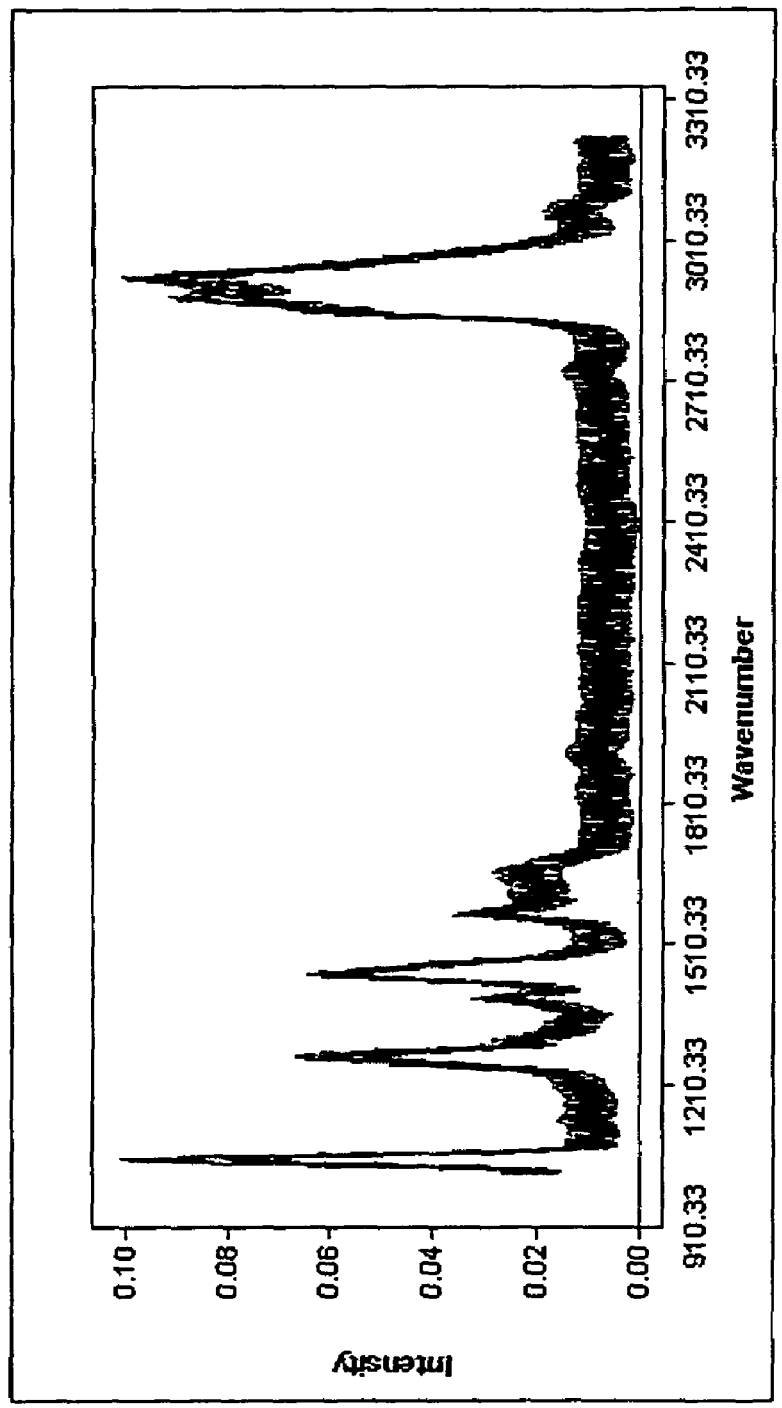
FIG. 2b is a spectral plot of all mixture spectra in a set of mathematically generated mixture spectra containing *Bacillus Pumilis, Bacillus Subtilis* and Baking Soda.
Figure 2C:
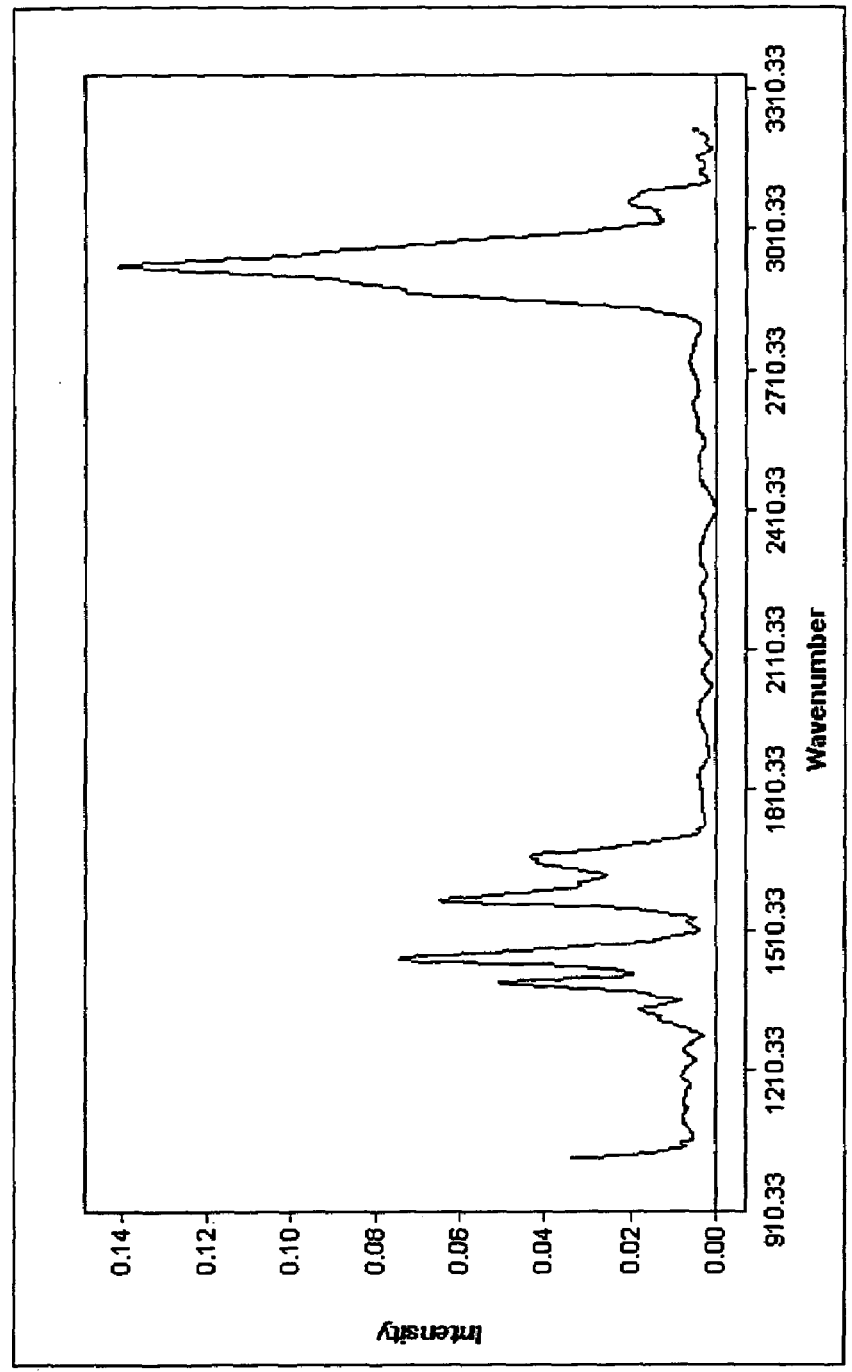
FIG. 2c is a spectral plot of *Bacillus Pumilis;*
Figure 2D:
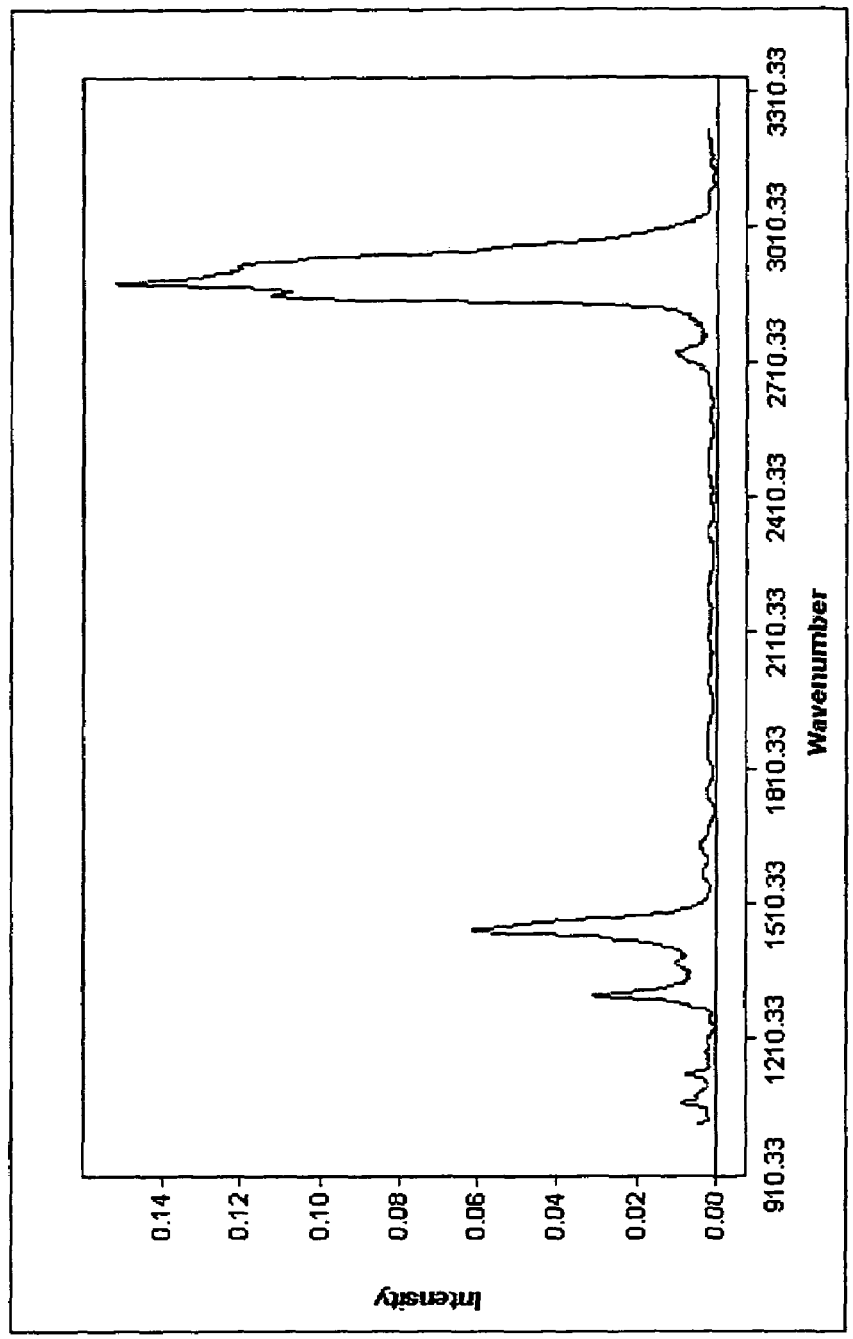
FIG. 2d is a spectral plot of *Bacillus Subtilis;*

FIGS. 2a-e illustrate the mixture spectra of Example 1 (FIGS. 2a and 2b), and the pure component spectra for *Bacillus Pumilis* (FIG. 2c), *Bacillus Subtilis* (FIG. 2d), and Baking Soda (FIG. 2e). One can see that the mixture spectrum shown in FIG. 2a (the first mixture spectrum) is significantly different from each of the individual pure component library spectrum as shown in FIGS. 2c-e. Comparing the collection of mixture spectra in FIGS. 2a and 2b illustrates that there is a variation in the peak intensities of the mixture spectra. The inventive method will work even with only a small amount of variation. Such variations can typically be achieved in real situations using data collection strategies that exploit, for example, sampling strategies or changes in magnification.

If one does a simple Euclidean Distance library search (a perfect match has a score of 100) for the Example 1 first mixture spectrum, the following matches are obtained.

TABLE 3

| Match | Score | Substance |
|---|---|---|
| 1 | 71.05 | *Bacillus Pumilis* |
| 2 | 70.88 | *Bacillus Anthracis* |
| 3 | 69.99 | Carboxymethyl Cellulose |
| 4 | 69.98 | *Clostridium Sporogenes* |
| 5 | 69.67 | *Bacillus Thuriengis* |
| 6 | 69.28 | *Bacillus Cereus* |
| 7 | 68.44 | Flour |
| 8 | 67.97 | Bisquick |
| 9 | 67.37 | *Bacillus Subtilis* |
| 10 | 66.74 | Corn Starch |
| 11 | 66.37 | Cane Sugar |
| 12 | 65.92 | Microcrystalline Cellulose |
| 13 | 63.33 | Sweet-n-Low |
| 14 | 60.58 | Dextrose |
| 15 | 55.74 | Talc |
| 16 | 55.01 | *Bacillus Stearothermophilus* |
| 17 | 54.51 | Baking Soda |
| 18 | 47.85 | Baking Power |

Thus, for Example 1, neither target factor testing nor a standard spectral library search gives the correct result. However, as shown above, the inventive method described herein correctly identified the components of the mixture.

EXAMPLE 1

Calculations

This section provides a set of calculations to illustrate the inventive method as applied to the mixture of Example 1. While this section will only describe the calculations for the identified best match of *Bacillus Pumilis, Bacillus Subtilis*, and Baking Soda, it should be understood that the same calculations will be performed for every possible combination of the top 10 matches (y=10) identified in Table 1.

Target factor testing yields the ranked matches provided in Table 1. One of the 1023 potential candidate solutions (subsets resulting from all possible combinations of the top 10 matches) is *Bacillus Pumilis, Bacillus Subtilis*, and Baking Soda. The projected library spectra are calculated as described above using Eqs. 4-6. The correlation coefficient CorrCoef is then calculated for each component in the candidate solution using the projected library spectra and the actual library spectra, as described in Eq. 7. The resulting values calculated using Eq. 7 are 0.8699, 0.8523, and 0.8845 for *Bacillus Pumilis, Bacillus Subtilis*, and Baking Soda, respectively. Using Eq. 8, the square root of the sum of the squares of these numbers, divided by 3.0, equals 0.8691. The test for negative concentrations is false (Eq. 9), so the *Bacillus Pumilis, Bacillus Subtilis*, and Baking Soda solution is not deleted. The last step of the inventive method (Eq. 10) is to square the cumulative correlation value (0.8691) and multiply it by the cumulative eigenvalues (0.4727 for three factors)—obtaining a corrected correlation coefficient value CorrectCorrCoef result of 0.3570.

EXAMPLE 2

Figure 3:
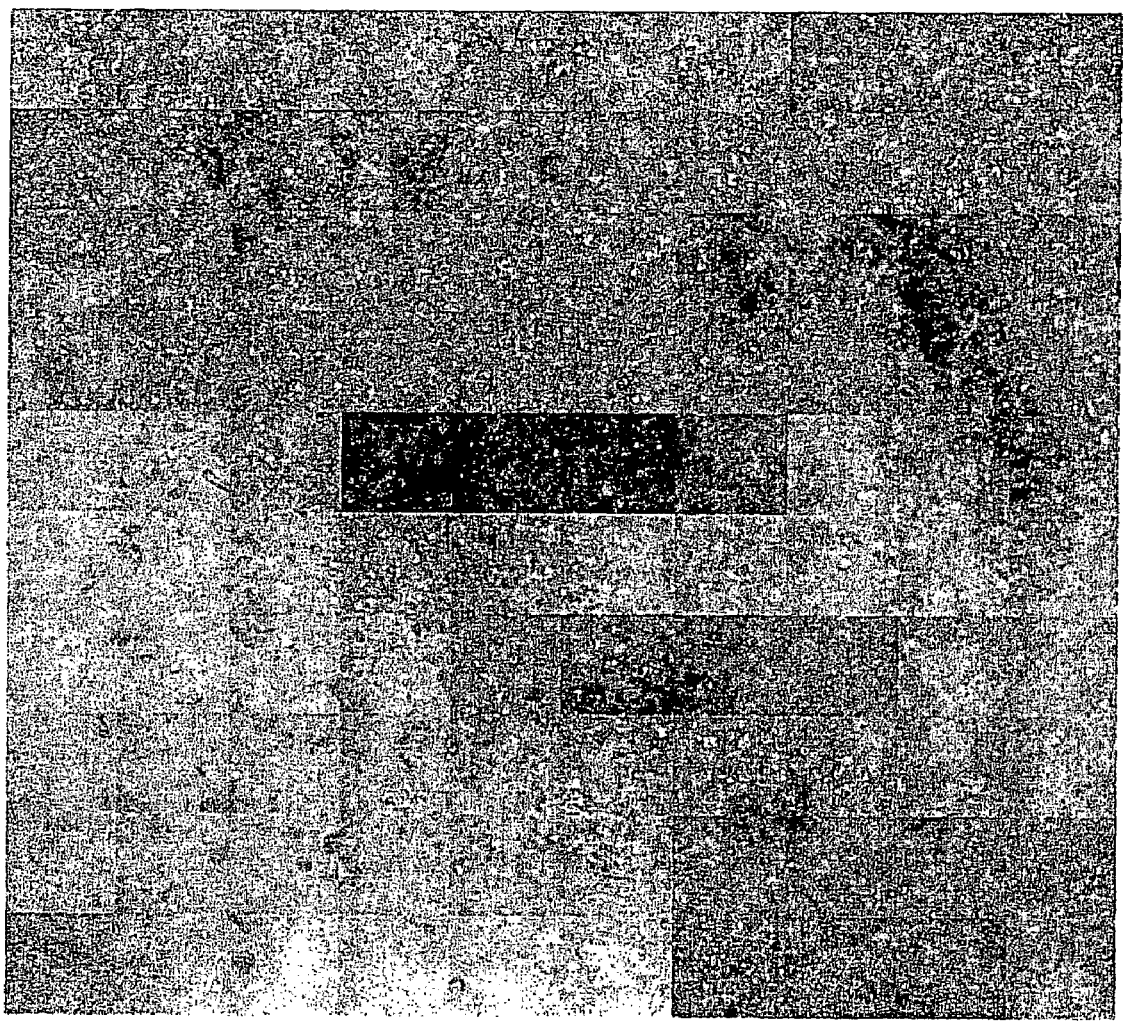
FIG. 3 is a physical image of the mixture of Microcrystalline Cellulose, Corn Starch, and Cane Sugar that is used for Example 2.

Another sample data set that has been tested contains a mixture of Cane Sugar, Microcystalline Cellulose, and Corn Starch, with equal amounts of Microcrystalline Cellulose and Corn Starch and three times that amount by weight of Cane Sugar. An image of this mixture is shown in FIG. 3, which is composed of 100 smaller images. Spectra from each of the 100 sample positions were collected (with 832 spectral points from 513.0 to 3450.0 $cm^{-1}$) and the inventive method applied to these spectra after applying a conventional instrumental response correction function to each spectrum. Target factor testing returned the top 10 matches (y=10), where an angle of 0-degrees represents a perfect match.

TABLE 4

| Spectral Library Entry | Angle |
|---|---|
| Microcystalline Cellulose | 11.06 |
| Corn Starch | 13.17 |
| Flour | 13.65 |
| Carboxymethyl Cellulose | 14.88 |
| Bisquick | 15.41 |
| *Bacillus Anthracis* in AK2 Media | 17.35 |
| Cane Sugar | 21.42 |
| *Bacillus Anthracis* in Sporulation Broth | 21.83 |
| *Bacillus Subtilis* | 26.63 |
| Acetaminophen | 26.91 |

As can be seen from Table 4, Cane Sugar is not among the top three matches. Thus, traditional target factor testing would result in an incorrect identification of the components of the mixture. Applying the remaining steps of the inventive method yield corrected correlation coefficient values CorrectCorrCoef of 0.5707, 0.7944, 0.8240, 0.8202, 0.7787, and 0.5867 as the top solutions for mixtures with one through six components, respectively (where a value of 1.0 represents a perfect match). The top five candidate solutions calculated in accordance with the inventive method are shown in Table 5 below.

TABLE 5

| Components | CCC Value |
|---|---|
| Microcrystalline Cellulose, Flour, Cane Sugar | 0.8240 |
| Microcrystalline Cellulose, Corn Starch, Cane Sugar | 0.8232 |
| Microcrystalline Cellulose, Bisquick, Cane Sugar | 0.8229 |
| Microcrystalline Cellulose, Corn Starch, Carboxymethyl Cellulose, Cane Sugar | 0.8202 |
| Microcrystalline Cellulose, Cane Sugar | 0.7944 |

As can be seen from Table 5, the three-component solution is predicted as the best solution, i.e., has the highest corrected correlation coefficient value CorrectCorrCoef. The top three solutions are three-component solutions, namely, (Microcrystalline Cellulose, Flour, Cane Sugar; Microcrystalline Cellulose, Corn Starch, Cane Sugar; and Microcrystalline Cellulose, Bisquick, Cane Sugar). Given the fact that the spectra of Flour, Corn Starch, and Bisquick are very similar, these solutions can be considered equivalent.

Figure 4A:
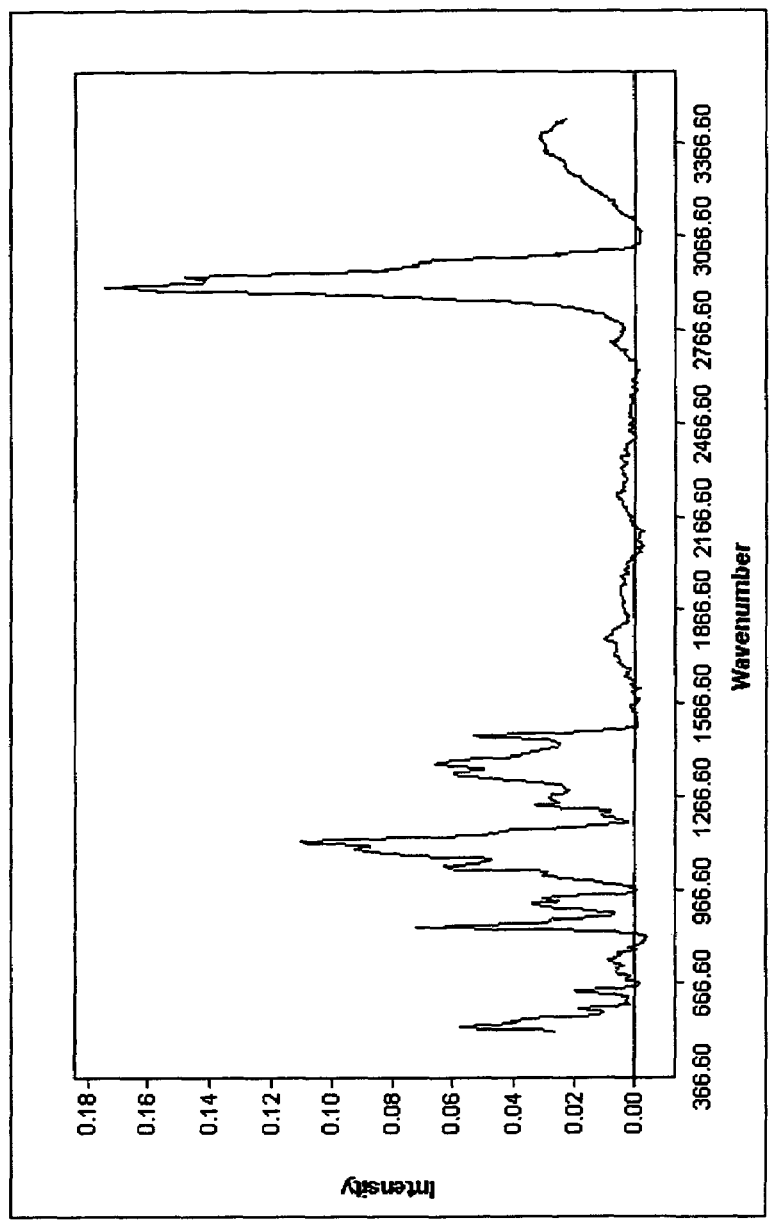
FIG. 4a is a spectral plot of a first mixture spectrum in a set of experimentally collected mixture spectra containing Microcrystalline Cellulose, Corn Starch, and Cane Sugar.
Figure 4B:
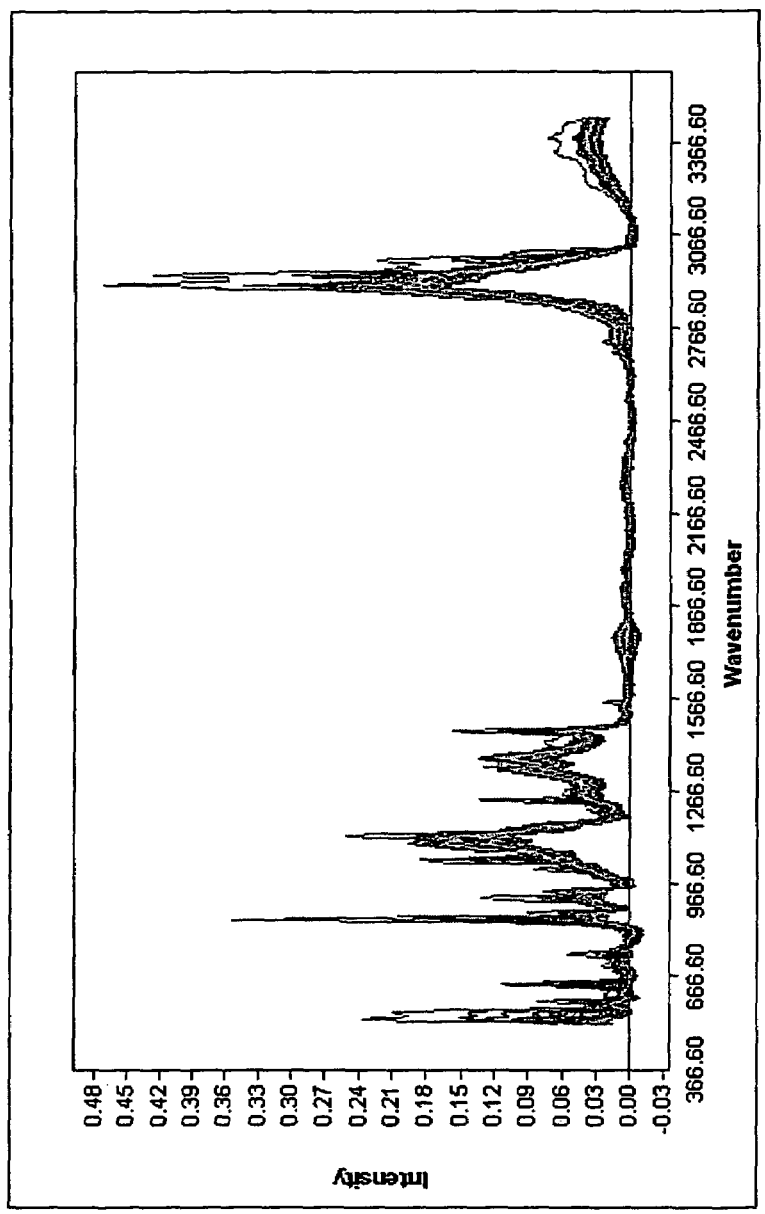
FIG. 4b is a spectral plot of all mixture spectra in a set of experimentally collected mixture spectra containing Microcrystalline Cellulose, Corn Starch, and Cane Sugar.
Figure 4C:
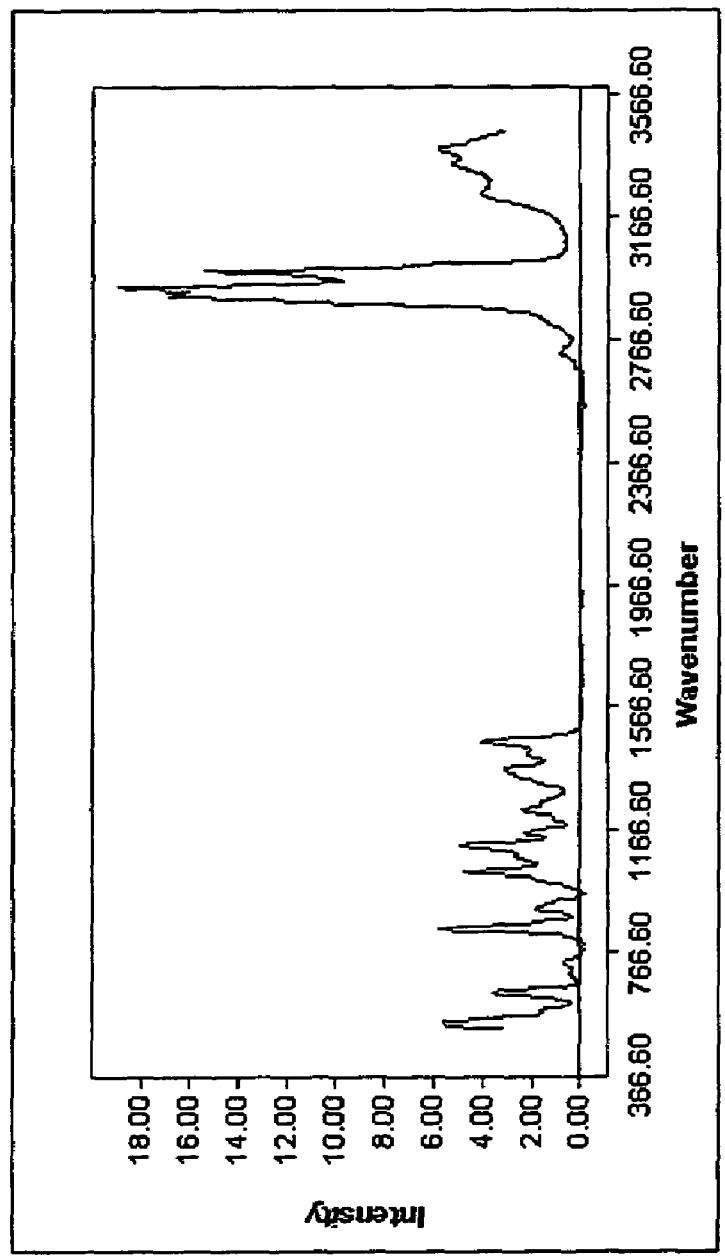
FIG. 4c is a spectral plot of Cane Sugar.
Figure 4D:
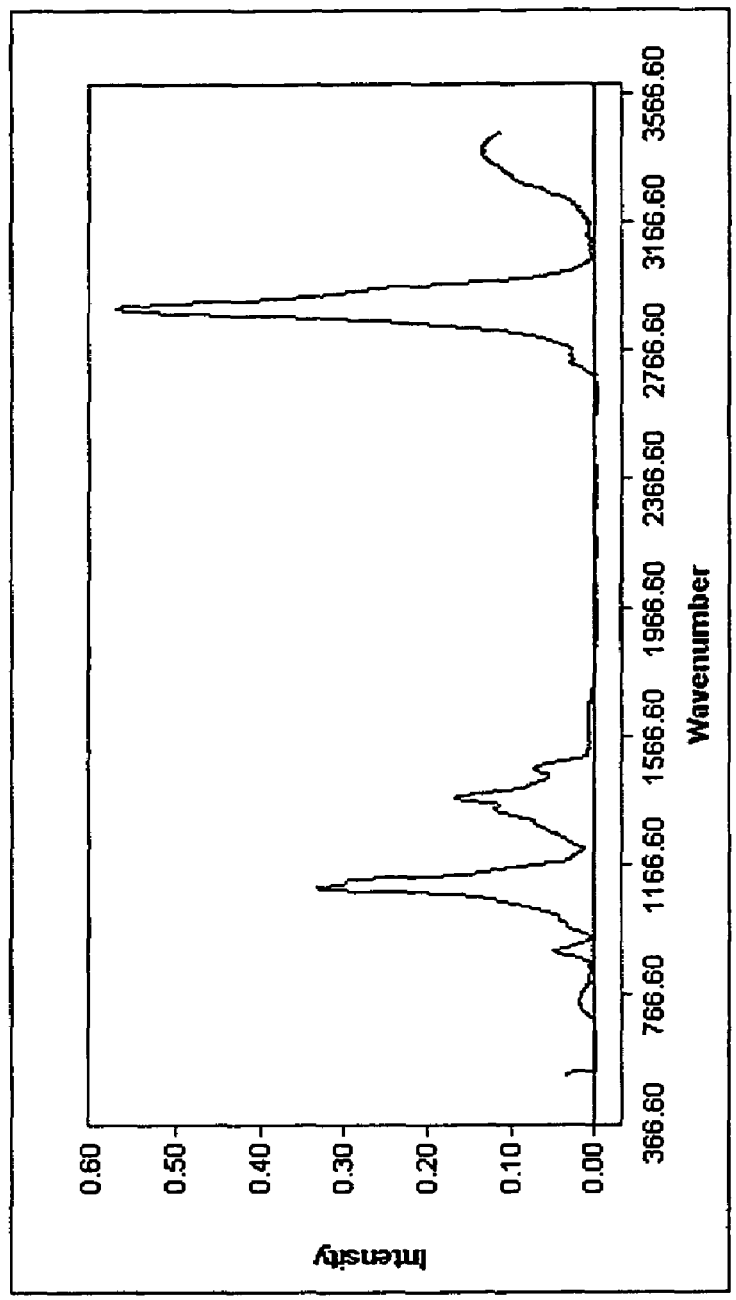
FIG. 4d is a spectral plot of Microcrystalline Cellulose.
Figure 4E:
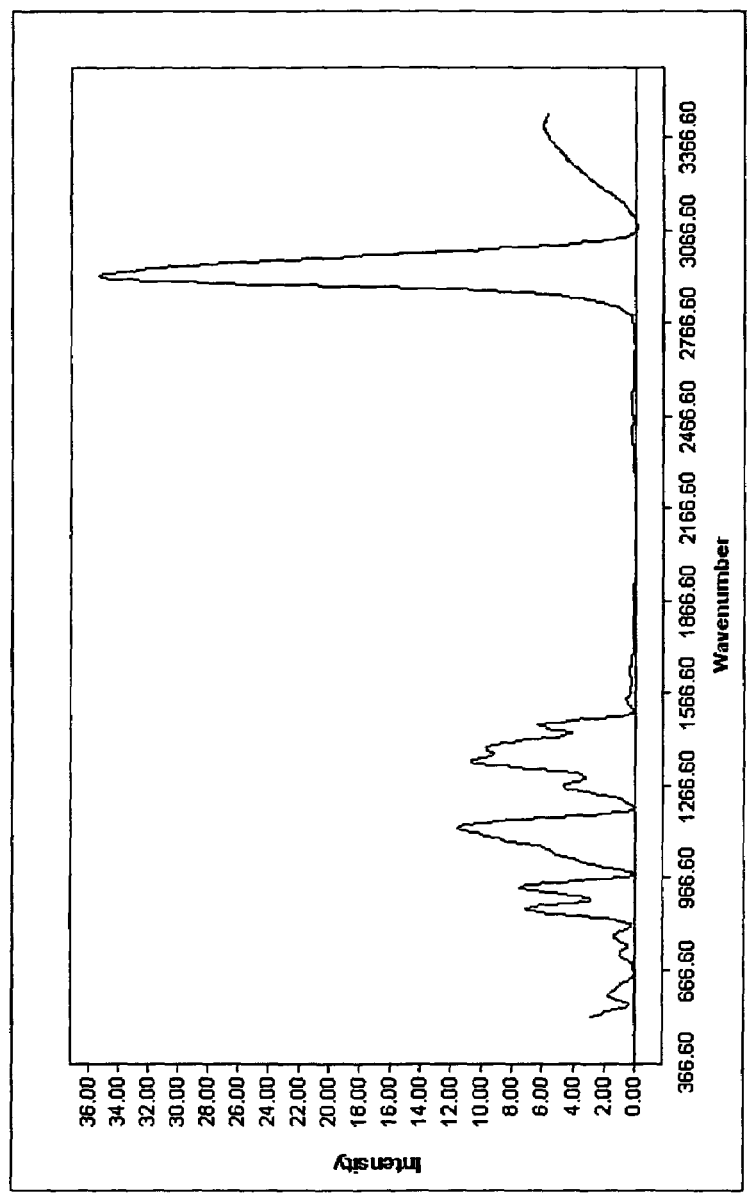
FIG. 4e is a spectral plot of Corn Starch.

FIGS. 4*a-e* illustrate the mixture spectra of Example 2 (FIGS. 4*a* and 4*b*), and the pure component spectra for Cane Sugar (FIG. 4*c*), Microcrystalline Cellulose (FIG. 4*d*), and Corn Starch (FIG. 4*e*). One can see that the mixture spectrum shown in FIG. 4*a* (the first mixture spectrum) is significantly different from each individual pure component library spectrum as shown in FIGS. 4*c-e*. Again, a comparison of FIGS. 4*a* and 4*b* illustrates some variation in the peak intensities of the mixture spectra, which will help to obtain a proper PCA model of this data set. As noted earlier, the inventive method with work with only a small amount of variation.

If one does a simple Euclidean Distance library search (a perfect match has a score of 100) for the Example 2 first mixture spectrum, the following matches are obtained.

TABLE 6

| Match | Score | Substance |
|---|---|---|
| 1 | 81.83 | Corn Starch |
| 2 | 81.25 | Microcrystalline Cellulose |
| 3 | 81.09 | Carboxymethyl Cellulose |
| 4 | 80.86 | All Purpose Flour |
| 5 | 79.99 | Low Fat Bisquick |
| 6 | 76.94 | Cane Sugar |
| 7 | 73.97 | Sweet-n-Low |
| 8 | 72.96 | *Bacillus Anthracis* in Ak2 media |
| 9 | 72.13 | Dextrose |
| 10 | 70.15 | BG Edgewood LD130_8 |
| 11 | 68.27 | *Bacillus Anthracis* in Sporulation Broth |
| 12 | 61.89 | *Bacillus Anthracis* in G media |
| 13 | 43.38 | Baking Powder |
| 14 | 41.69 | Acetaminophen |
| 15 | 39.68 | Baking Soda |
| 16 | 33.01 | Talc |

Thus, for Example 2, neither target factor testing nor a standard spectral library search gives the correct result. However, as shown above, the inventive method described herein correctly identified the components of the mixture, given that Corn Starch, Flour, and Bisquick are considered in the library to be equivalent components.

EXAMPLE 2

Calculations

This section provides a set of calculations to illustrate the inventive method as applied to the mixture of Example 2.

While this section will only describe the calculations for one of the top three identified best matches of Microcrystalline Cellulose, Corn Starch, and Cane Sugar it should be understood that the same calculations will be performed for every possible combination of the top 10 matches (y=10) identified in Table 4.

Target factor testing yields the ranked matches provided in Table 4. One of the 1023 potential candidate solutions (subsets resulting from all possible combinations of the top 10 matches) is Microcrystalline Cellulose, Corn Starch, and Cane Sugar. The projected library spectra are calculated as described above using Eqs. 4-6. The correlation coefficient CorrCoef is then calculated for each component in the candidate solution using the projected library spectra and the actual library spectra, as described in Eq. 7. The resulting values calculated using Eq. 7 are 0.9588, 0.9564, and 0.8669 for Microcrystalline Cellulose, Corn Starch, and Cane Sugar, respectively. Using Eq. 8, the square root of the sum of the squares of these numbers, divided by 3.0, equals 0.9284. The test for negative concentrations is false (Eq. 9), so the Microcrystalline Cellulose, Corn Starch, and Cane Sugar solution is not deleted. The last step of the inventive method (Eq. 10) is to square the cumulative correlation value (0.9284) and multiply it by the cumulative eigenvalues (0.9551 for three factors)—obtaining a corrected correlation coefficient value CorrectCorrCoef result of 0.8232, which is one of the top three matches given that Corn Starch, Flour, and Bisquick are considered equivalent.

The inventive method of spectral unmixing described herein is not only more accurate than conventional spectral unmixing methods, but can also be rapidly applied in a variety of situations. The speed at which the inventive method obtains the ranking criterion, i.e., the corrected correlation coefficient value CorrectCorrCoef, and thus identifies the components of the mixture, allows one to capture and analyze data sequentially as time dependent changes occur in the sample. Such time dependent changes may arise in situations where the sampling of a mixture or object occurs in defined time intervals, such as, for example, in an air sampling system.

In one type of air sampling system, air samples are sprayed onto a small, moving belt, with different positions on the belt corresponding to different time periods. For example, air sprayed onto the moving belt at a first point in time will be sprayed at a first position on the belt, while air sprayed onto the moving belt at a later point in time will be sprayed at a second position on the belt. Collecting sets of spectral data at the first and second positions on the belt allows an analyst to monitor trends in the composition of the air, particulates or other chemicals in the air that are being analyzed over the time interval defined by the first and second positions on the moving belt. For example, obtaining a set of spectral data from the first position on the belt allows an analyst, via the inventive spectral unmixing method described herein, to determine the composition of the air sample at the first point in time. Then, obtaining a set of spectral data from the second position on the belt allows the analyst, via the inventive spectral unmixing method described herein, to determine the composition of the air sample at the second, later point in time. The speed of the inventive spectral unmixing method is such that the analyst is readily provided with the air sample compositions at the first and second points in time, such that the analyst can analyze the air, particulates or other chemical compounds in the air and observe trends in the composition of these air samples during the time interval between the first and second points in time. In this manner, the inventive spectral unmixing method described herein can be utilized in dynamic spectral unmixing applications where changes in composition over time are analyzed.

It should be understood that the air sampling system described above is provided for exemplary purposes only. The dynamic nature of the inventive spectral unmixing method can be utilized in any application or situation where the sampling of a mixture or object (gas, liquid, solid, powder, etc.) occurs in defined timed intervals. Monitoring the dynamic changes in the corrected correlation coefficient value CorrectCorrCoef, and thus the changes in the composition of the mixture, provides an analyst with further information to distinguish small random noise variations, i.e., sampling variations, from the trends exhibited by the mixture or object being analyzed. Different situations will dictate what trends are reasonable and anticipated. Those trends that are unexpected in a given situation can have implications that are particularly significant and of value for early warning and/or process control. Such situations where the dynamic nature of the inventive spectral unmixing method can be fully realized include, but are not limited to, situations such as product or chemical manufacturing, patient monitoring and clinical diagnostics, as well as biothreat or hazardous chemical monitoring.

Additionally, the set of spectral data obtained from the mixture and utilized by the present invention to determine the composition of the mixture can include combined spectral data sets obtained from the mixture at different points in time. For example, different sets of spectral data can be obtained from the mixture at different points in time, with the different sets of spectral data combined into a combined spectral data set. The inventive spectral unmixing method described herein is applied to the combined spectral data set to determine the composition of the mixture. By combining the spectral data sets obtained from the mixture at different points in time, one can obtain more accurate results than if each of the spectral data sets were analyzed individually.

Similarly, this method can be applied to a mixture which may change over time such as, for example, a drug tablet exposed to a solvent. In other cases, the time dependent spectral changes may correspond to spatial variations as the sample is moved and spectra are sequentially taken.

The method of the present invention provides an accurate and rapid means of identifying the components of a mixture (gas, liquid, solid, powder, etc.). The examples provided above attest to its reliability. While the present invention has been described with particular reference to the drawings, it should be understood that various modifications could be made without departing with the spirit and scope of the present invention. For example, while target factor testing has been described herein as a technique for ranking a plurality of library spectra of known elements based on their likelihood of being a component of the mixture, any technique which provides such a ranking of library spectra can be utilized with departing from the spirit and scope of the present invention. Additionally, while various steps and equations have been described herein for determining the correlation coefficient CorrCoef, the cumulative correlation coefficient CumCorrCoef, and the corrected correlation coefficient CorrectCorrCoef values, any step(s) or equation(s) that results in a similar ranking of the candidate solutions may be utilized in accordance with the teachings of the present invention without departing from the spirit and scope of the present invention.

We claim:

1. A method of identifying components of a mixture, said method comprising the steps of:
   obtaining a set of spectral data from a mixture, wherein said spectral data are obtained at a spatial resolution sufficient to resolve non-uniformities in said mixture;
   ranking, based on the set of spectral data, a plurality of library spectra of known elements; and
   calculating a corrected correlation coefficient for each combination of the top y ranked library spectra to thereby identify components of a mixture.

2. The method of claim 1, wherein the plurality of library spectra of known elements are ranked according to their angle of projection into the set of spectral data, and using target factor testing techniques.

3. The method of claim 1, wherein the step of calculating a corrected correlation coefficient for each combination of the top y ranked library spectra comprises the steps of:
   calculating a correlation coefficient for each known element included in a given combination;
   combining the correlation coefficients for the known elements included in the given combination to develop a cumulative correlation coefficient value;
   developing cumulative eigenvalues for the given combination; and
   multiplying the cumulative correlation coefficient value by the cumulative eigenvalues to develop the corrected correlation coefficient for the given combination.

4. The method of claim 3, wherein the step of combining the correlation coefficients comprises the step of calculating the square root of the sum of the squares of the correlation coefficients for the known elements included in the given combination to develop the cumulative correlation coefficient for the given combination.

5. The method of claim 3, wherein the step of combining the correlation coefficients comprises the step of calculating the square root of the sum of the squares of the correlation coefficients for the known elements included in the given combination divided by the number of known elements included in the given combination to develop the cumulative correlation coefficient for the given combination.

6. The method of claim 3, wherein the step of calculating a correlation coefficient comprises the steps of:
   calculating a projected library spectrum for each known element included in the given combination; and
   measuring the similarity of the projected library spectrum with its actual library spectrum to develop the correlation coefficient for each known element in the given combination.

7. The method of claim 6, wherein the step of measuring the similarity of the projected library spectrum with its actual library spectrum comprises the steps of:
   calculating the dot product of the projected library spectrum with the actual library spectrum; and
   dividing the calculated dot product by the multiplication of the dot product of the projected library spectrum with itself and the dot product of the actual library spectrum with itself to develop the correlation coefficient for each known element in the given combination.

8. The method of claim 6, wherein the step of calculating a projected library spectrum comprises the steps of:
   using the obtained set of spectral data for the mixture and the library spectra of known elements to calculate relative concentrations of each known element included in the given combination; and
   using the calculated relative concentrations and the obtained set of spectral data for the mixture to calculate the projected library spectrum for each known element included in the given combination.

9. The method of claim 8, wherein if any known element in the given combination is calculated to have a negative relative concentration, eliminating the given combination from consideration.

10. The method of claim 8, wherein if any known element in the given combination is calculated to have a negative relative concentration:
calculating the ratio of a maximum positive calculated relative concentration for the given combination to the average of the sum of the absolute values of the calculated negative relative concentrations for the given combination; and
if the calculated ratio is less than a predetermined number, eliminating the given combination from consideration.

11. The method of claim 8, wherein if any known element in the given combination is calculated to have a negative relative concentration:
calculating the ratio of a maximum positive calculated relative concentration for the given combination to the average of the sum of the absolute values of the calculated negative relative concentrations divided by the number of concentrations that are negative for the given combination; and
if the calculated ratio is less than a predetermined number, eliminating the given combination from consideration.

12. The method of claim 11, wherein the predetermined number comprises 4.0.

13. The method of claim 1, wherein y is equal to 10.

14. The method of claim 1, wherein the plurality of library spectra of known elements are ranked according to their angle of projection into the set of spectral data, from smallest to largest.

15. The method of claim 1, further comprising the step of correcting the set of spectral data to remove signals and information not due to the chemical composition of the mixture.

16. The method of claim 1, further comprising the steps of:
obtaining, at a later point in time, another set of spectral data from the mixture, such that the another set of spectral data is separated from the set of spectral data by a time interval, and wherein said another set of spectral data are obtained at a spatial resolution sufficient to resolve non-uniformities in said mixture;
ranking, based on the another set of spectral data, said plurality of library spectra of known elements;
calculating another corrected correlation coefficient for each another combination of the top y ranked library spectra.

17. The method of claim 16, further comprising the steps of:
selecting the combination having the highest corrected correlation coefficient, wherein the known elements of the selected combination are identified as the components of the mixture at the earlier point in time;
selecting the another combination having the highest corrected correlation coefficient, wherein the known elements of the another selected combination are identified as the components of the mixture at the later point in time; and
using the identified components of the mixture from both the set of spectral data and the another set of spectral data to analyze trends in the composition of the mixture over the time interval.

18. The method of claim 1, wherein the set of spectral data comprises a plurality of spectral data sets obtained from the mixture at different points in time.

19. The method of claim 1, wherein the set of spectral data comprises a plurality of spectral data sets obtained from the mixture at different locations in the mixture.

20. A method of identifying components of a mixture from a set of spectral data obtained from the mixture, said spectral data being obtained at a spatial resolution sufficient to resolve non-uniformities in said mixture, and defining a mixture data space, said method comprising the steps of:
ranking, based on the set of spectral data, a plurality of library spectra of known elements; and
calculating a ranking criterion for each combination of the top y ranked library spectra to thereby identify components of a mixture.

21. The method of claim 20, where the plurality of library spectra are ranked based on at least one of their angle of projection into the mixture data space and their likelihood of being a component of the mixture.

22. The method of claim 20, wherein the ranking criterion comprises a corrected correlation coefficient for each combination, and wherein the combination having the highest corrected correlation coefficient is selected, and the known elements of the selected combination are identified as the components of the mixture.

23. The method of claim 22, wherein the step of calculating a ranking criterion for each combination of the top y ranked library spectra comprises the steps of:
calculating a correlation coefficient for each known element included in a given combination;
combining the correlation coefficients for the known elements included in the given combination to develop a cumulative correlation coefficient value;
squaring the cumulative correlation coefficient value;
developing cumulative eigenvalues for the given combination; and
multiplying the squared cumulative correlation coefficient value by the cumulative eigenvalues to develop the corrected correlation coefficient for the given combination.

24. The method of claim 23, wherein the step of calculating a correlation coefficient comprises the steps of:
calculating a projected library spectrum for each known element included in the given combination; and
measuring the similarity of the projected library spectrum with its actual library spectrum to develop the correlation coefficient for each known element in the given combination.

25. The method of claim 24, wherein the step of calculating a projected library spectrum comprises the steps of:
using the obtained spectral data and the known library spectra to calculate relative concentrations of each known element included in the given combination; and
using the calculated relative concentrations and the obtained spectral data to calculate the projected library spectrum for each known element included in the given combination,
wherein if any known element in the given combination is calculated to have a negative relative concentration:
calculating the ratio of a maximum positive calculated relative concentration for the given combination to the average of the sum of the absolute values of the calculated negative relative concentrations divided by the number of concentrations that are negative for the given combination; and if the calculated ratio is less than a predetermined number, eliminating the given combination from consideration.

26. The method of claim 20, further comprising the steps of:
   obtaining, at a later point in time, another set of spectral data from the mixture, such that the another set of spectral data is separated from the set of spectral data by a time interval, the another set of spectral data defining another mixture data space and wherein said another set of spectral data are obtained at a spatial resolution sufficient to resolve non-uniformities in said mixture;
   ranking, based on the another set of spectral data, said plurality of library spectra of known elements according to the likelihood of said known elements being a component of the mixture, from most likely to least likely;
   calculating a ranking criterion for each combination of the top y ranked library spectra; and
   selecting a combination based on the ranking criterion, wherein the known elements of the selected combination are identified as the components of the mixture at the later point in time.

27. The method of claim 26, further comprising the step of using the identified components of the mixture from both the set of spectral data and the another set of spectral data to analyze trends in the composition of the mixture over the time interval.

28. The method of claim 26, wherein the ranking criterion comprises a corrected correlation coefficient, and wherein the step of selecting a combination based on the ranking criterion comprises the step of selecting the combination having the highest corrected correlation coefficient, wherein the known elements of the selected combination are identified as the components of the mixture.

29. The method of claim 20, further comprising the steps of:
   obtaining another set of spectral data from the mixture at a location different from the location of the set of spectral data, the another set of spectral data defining another mixture data space;
   ranking, based on the another set of spectral data, said plurality of library spectra of known elements according to the likelihood of the known elements being a component of the mixture, from most likely to least likely;
   calculating a ranking criterion for each combination of the top y ranked library spectra; and
   selecting a combination based on the ranking criterion, wherein the known elements of the selected combination are identified as the components of the mixture at the different location.

30. The method of claim 29, further comprising the step of using the identified components of the mixture from both the set of spectral data and the another set of spectral data to analyze trends in the composition of the mixture over its spatial area.

31. A method of identifying components of a mixture, said method comprising the steps of:
   representing a mixture as an image, wherein said image includes a plurality of sub-images, wherein each sub-image corresponds to a respective portion of said mixture;
   obtaining a corresponding set of spectral data for at least one sub-image, wherein said set of spectral data is obtained at a spatial resolution sufficient to resolve non-uniformities in said mixture;
   ranking, based on the set of spectral data, a plurality of library spectra of known elements according to the likelihood of the known elements being a component of said mixture, from most likely to least likely; and
   calculating a ranking criterion for each combination of the top y ranked library spectra.

32. The method of claim 31, wherein a combination of all sets of spectral data define a mixture data space, and wherein said ranking step includes:
   ranking the plurality of library spectra of known elements according to the spectrum-specific angle of projection of the spectra of the known elements into the mixture data space.

33. A method of identifying components of a mixture, said method comprising the steps of:
   obtaining a set of spectral data of a mixture, wherein said spectral data are obtained at a spatial resolution sufficient to resolve non-uniformities in said mixture;
   ranking, based on the set of spectral data, a plurality of library spectra of known elements according to the likelihood of the known elements being a component of said mixture, from most likely to least likely;
   calculating a ranking criterion of each combination of the top y ranked library spectra; and
   identifying components of interest of said mixture by selecting a combination of the top y ranked library spectra, based on the ranking criterion, wherein said combination includes library spectra of only those known elements that constitute the components of interest.

34. A method of identifying components of a mixture, said method comprising the steps of:
   obtaining a first set of spectral data from a mixture, wherein said first set of spectral data is obtained at a spatial resolution sufficient to resolve non-uniformities in said mixture;
   ranking, based on said first set of spectral data, a first plurality of library spectra of known elements according to the likelihood of an element being a component of the mixture, from most likely to least likely;
   calculating a first ranking criterion for each combination of the top y ranked library spectra from said first plurality of library spectra;
   selecting a first combination based on the first ranking criterion, wherein the known elements of the selected first combination are identified as a first set of components of said mixture;
   obtaining, at a different point in time, a second set of spectral data from said mixture, wherein said second set of spectral data is obtained at a spatial resolution sufficient to resolve non-uniformities in said mixture;
   ranking, based on said second set of spectral data, a second plurality of library spectra of known elements according to the likelihood of an element being a component of said mixture, from most likely to least likely;
   calculating a second ranking criterion for each combination of the top y ranked library spectra from said second plurality of library spectra;
   selecting a second combination based on the second ranking criterion, wherein the known elements of the selected second combination are identified as a second set of components of said mixture; and
   detecting a time-varying anomaly in the composition of said mixture based on identification of said first and said second sets of components of said mixture.

35. A method of identifying components of a mixture, said method comprising the steps of:
- obtaining a first set of spectral data from a mixture, wherein said first set of spectral data is obtained at a spatial resolution sufficient to resolve non-uniformities in said mixture;
- obtaining, at a different point in time, a second set of spectral data from said mixture, wherein said second set of spectral data is obtained at a spatial resolution sufficient to resolve non-uniformities in said mixture;
- combining at least a portion of said first set and at least a portion of said second set of spectral data into a combined set of spectral data;
- ranking, based on said combined set of spectral data, a plurality of library spectra of known elements according to the likelihood of an element being a component of the mixture, from most likely to least likely; and
- calculating a ranking criterion for each combination of the top y ranked library spectra from said plurality of library spectra.

36. An apparatus to identify components of a mixture comprising:
- a computing device to represent a mixture as an image, wherein said image includes a plurality of sub-images, wherein each sub-image corresponds to a respective portion of said mixture, and
- wherein a corresponding set of spectral data is obtained from at least one sub-image, wherein said set of spectral data are obtained at a spatial resolution sufficient to resolve non-uniformities in said mixture, and
- wherein a plurality of library spectra of known elements are ranked based on the set of spectral data according to their likelihood of being a component of said mixture, from most likely to least likely, and
- wherein a ranking criterion is calculated for each combination of the top y ranked library spectra.

* * * * *